(12) United States Patent
Girlando et al.

(10) Patent No.: US 9,678,027 B2
(45) Date of Patent: Jun. 13, 2017

(54) MONITORING DEVICE WITH JUMPER CABLE COUPLING AND RELATED METHODS

(71) Applicant: STMICROELECTRONICS S.r.l., Agrate Brianza (IT)

(72) Inventors: Giovanni Girlando, Catania (IT); Michele Calabretta, Giarre (IT); Francesco Pappalardo, Paterno (IT)

(73) Assignee: STMICROELECTRONICS S.R.L., Agrate Brianza (MB) (IT)

( * ) Notice: Subject to any disclaimer, the term of this patent is extended or adjusted under 35 U.S.C. 154(b) by 279 days.

(21) Appl. No.: 14/670,613

(22) Filed: Mar. 27, 2015

(65) Prior Publication Data

US 2015/0253268 A1    Sep. 10, 2015

Related U.S. Application Data

(63) Continuation-in-part of application No. 13/770,492, filed on Feb. 19, 2013, now Pat. No. 9,335,286.

(30) Foreign Application Priority Data

Feb. 29, 2012  (IT) .............................. MI2012A0309

(51) Int. Cl.
*G01N 27/20* (2006.01)
*G01N 27/00* (2006.01)
(Continued)

(52) U.S. Cl.
CPC .......... *G01N 27/00* (2013.01); *G01M 5/0033* (2013.01); *G01M 5/0083* (2013.01); *H04Q 9/00* (2013.01); *H04Q 2209/88* (2013.01)

(58) Field of Classification Search
CPC ................ G01N 27/20; G01N 27/041; G01N 2291/105; G01N 2291/2623;
(Continued)

(56) References Cited

U.S. PATENT DOCUMENTS

2004/0153270 A1*  8/2004  Yamashita ........... G01N 33/383
                                                                    702/81
2005/0204825 A1   9/2005  Kunerth et al.
(Continued)

FOREIGN PATENT DOCUMENTS

EP          2469866 A2     6/2012
GB          2426669 A     11/2006
WO       2012084295 A1    6/2012

*Primary Examiner* — Patrick Assouad
*Assistant Examiner* — Taqi Nasir
(74) *Attorney, Agent, or Firm* — Slater Matsil, LLP

(57) ABSTRACT

A monitoring device is for a block of building material. The monitoring device may include an electric supply line configured to be buried in the block of building material and having a flexible main cable, and flexible jumper cables coupled to the flexible main cable and extending outwardly. The monitoring device may include sensor devices configured to be buried in the block of building material and coupled to respective ones of the flexible jumper cables. Each sensor device may include a primary inductor coupled to the electric supply line at a position based upon peaks of a stationary waveform when the electric supply line is alternating current (AC) powered, and a monitoring circuit. The monitoring circuit may include an integrated sensor, and a secondary inductor magnetically coupled to the primary inductor and configured to supply the integrated sensor, and communicate through the electric supply line.

20 Claims, 7 Drawing Sheets

(51) Int. Cl.
*G01M 5/00* (2006.01)
*H04Q 9/00* (2006.01)

(58) Field of Classification Search
CPC ... G01N 2291/2636; G01N 2291/2675; G01N
25/56; H04W 76/023; H04W 24/10;
H04W 24/02; H04W 12/06; H04W 24/08;
H04W 12/04; H04W 84/18; G08B 13/12;
G08B 13/14; G08B 13/1427; G08B
13/22; G08B 13/24; G08B 13/2402;
G05B 19/418; G05B 2219/32222; G05B
2219/34477; G05B 2219/37021
USPC ....... 324/600, 649, 654, 655, 656, 657, 663,
324/693, 699, 700, 702, 715, 718, 722,
324/71.1, 71.2; 340/540, 665, 505,
340/539.26, 538.86, 870.31; 702/81,
702/33–35; 73/86, 786; 455/41.1, 67.11
See application file for complete search history.

(56) References Cited

U.S. PATENT DOCUMENTS

| | | | |
|---|---|---|---|
| 2008/0036476 A1* | 2/2008 | Nielsen | G01N 17/02 324/700 |
| 2010/0117665 A1* | 5/2010 | Sorrentino | C08J 3/248 324/693 |
| 2012/0038346 A1* | 2/2012 | Beuk | B05B 5/1683 324/71.1 |
| 2012/0161789 A1* | 6/2012 | Girlando | G01N 33/38 324/655 |
| 2013/0221945 A1* | 8/2013 | Girlando | G01N 27/00 324/71.1 |

* cited by examiner

MONITORING DEVICE WITH JUMPER CABLE COUPLING AND RELATED METHODS

RELATED APPLICATION

This application is based upon prior filed copending application Ser. No. 13/770,492 filed Feb. 19, 2013, the entire subject matter of which is incorporated herein by reference in its entirety.

TECHNICAL FIELD

This present disclosure relates to monitoring devices and, more particularly, to a monitoring device and related method for use in a building structure.

BACKGROUND

The strategy for implementing damage detection and the characterization of mechanical structures is commonly called Structural Health Monitoring (SHM). Damages are defined as modifications of the material and/or of the geometrical properties of a structural system, comprising modifications of boundary conditions and connections of the system, that worsen performance of the system. The SHM process implies the observation of the mechanical system over time using periodically: measurements of dynamic responses coming from an array of sensors, extraction of data of damage characteristics sensed from these measurements, and statistical analysis of these data of damage characteristics for determining the present health state of the system (also called structural analysis).

This process provides information about the capacity of the structure for carrying out its function, considering the unavoidable aging and degradation in working environments. After extreme events, such as earthquakes or explosions, the SHM is used for a quick screening of the conditions of the structure for providing, almost in real time, reliable information about the integrity of the structure itself.

Currently, SHM systems use sensors placed on the surfaces to be monitored. For example, sensors used (anemometers for calculating the wind speed, accelerometers, extensometers, motion transducers, temperature sensors, sensors for detecting motion of weights, etc.) for monitoring bridges are placed on the external surfaces of beams, ropes or pillars. This is done to: estimate the effects of loads on the bridge, evaluate the weakening of the bridge, and foresee the probable evolution of the bridge and its expected lifetime.

SHM systems with sensors to be buried in the building structure to be monitored have been devised. These sensors (pressure, humidity, temperature, etc.) have at least one remote powering and transmission antenna for transmitting the measured values outside of the block of building material. These kinds of sensors are disclosed, for example, in U.S. patent application No. 2004/0153270 and in Italian patent applications VA2010A000097 and MI2010A002365.

An inconvenience of the monitoring circuits to be buried in the building material includes the difficulties of powering them. In Italian patent application No. VA2010A000097, each monitoring circuit is powered through a magnetic coupling with an inductor connected to a shielded line, as shown in FIG. 1. In Italian patent application No. MI2010A002365 the monitoring circuits are fixed to a linear support, as shown in FIG. 2, and have remote powering antennas that receive the electromagnetic field irradiated by an external power supply.

SUMMARY

Generally, a monitoring device is for a block of building material and may include an electric supply line configured to be buried in the block of building material and comprising a flexible main cable, and a plurality of flexible jumper cables coupled to the flexible main cable and extending outwardly therefrom. The monitoring device may include a plurality of sensor devices configured to be buried in the block of building material and coupled to respective ones of the plurality of flexible jumper cables. Each sensor device may include a primary inductor coupled to the electric supply line at a position based upon peaks of at least one stationary waveform when the electric supply line is alternating current (AC) powered, and a monitoring circuit. The monitoring circuit may include an integrated sensor, and a secondary inductor magnetically coupled to the primary inductor and configured to supply the integrated sensor, and communicate through the electric supply line.

In particular, the flexible main cable and the plurality of flexible jumper cables may each comprise a coaxial cable portion. The electric supply line may comprise a plurality of connectors (e.g. T-connector) coupling the respective ones of the plurality of flexible jumper cables to the flexible main cable.

In some embodiments, the electric supply line may comprise a plurality of encapsulation layers respectively surrounding the plurality of connectors. The monitoring device may further comprise an antenna coupled to the electric supply line and configured to be remotely powered and transmit sensed values of at least one physical characteristic.

Also, at least one of the primary inductors may be electrically coupled in series with the electric supply line in correspondence with peaks of a current stationary waveform. At least one of the primary inductors may be electrically coupled in parallel with the electric supply line in correspondence with peaks of a voltage stationary waveform. The monitoring device may further include a resonant network coupled to at least one of the primary inductors.

Another aspect is directed to a method for making a monitoring device for a block of building material. The method may include providing an electric supply line to be buried in the block of building material and comprising a flexible main cable, and a plurality of flexible jumper cables coupled to the flexible main cable and extending outwardly therefrom. The method may include coupling a plurality of sensor devices to respective ones of the plurality of flexible jumper cables. Each sensor device may comprise a primary inductor coupled to the electric supply line at a position based upon peaks of at least one stationary waveform when the electric supply line is AC powered, and a monitoring circuit. The monitoring circuit may include an integrated sensor, and a secondary inductor magnetically coupled to the primary inductor and to supply the integrated sensor, and communicate through the electric supply line.

DETAILED DESCRIPTION

The present disclosure will now be described more fully hereinafter with reference to the accompanying drawings, in which several embodiments of the invention are shown. This present disclosure may, however, be embodied in many different forms and should not be construed as limited to the embodiments set forth herein. Rather, these embodiments are provided so that this disclosure will be thorough and complete, and will fully convey the scope of the present disclosure to those skilled in the art. Like numbers refer to like elements throughout, and prime notation is used to indicate similar elements in alternative embodiments.

Figure 1:
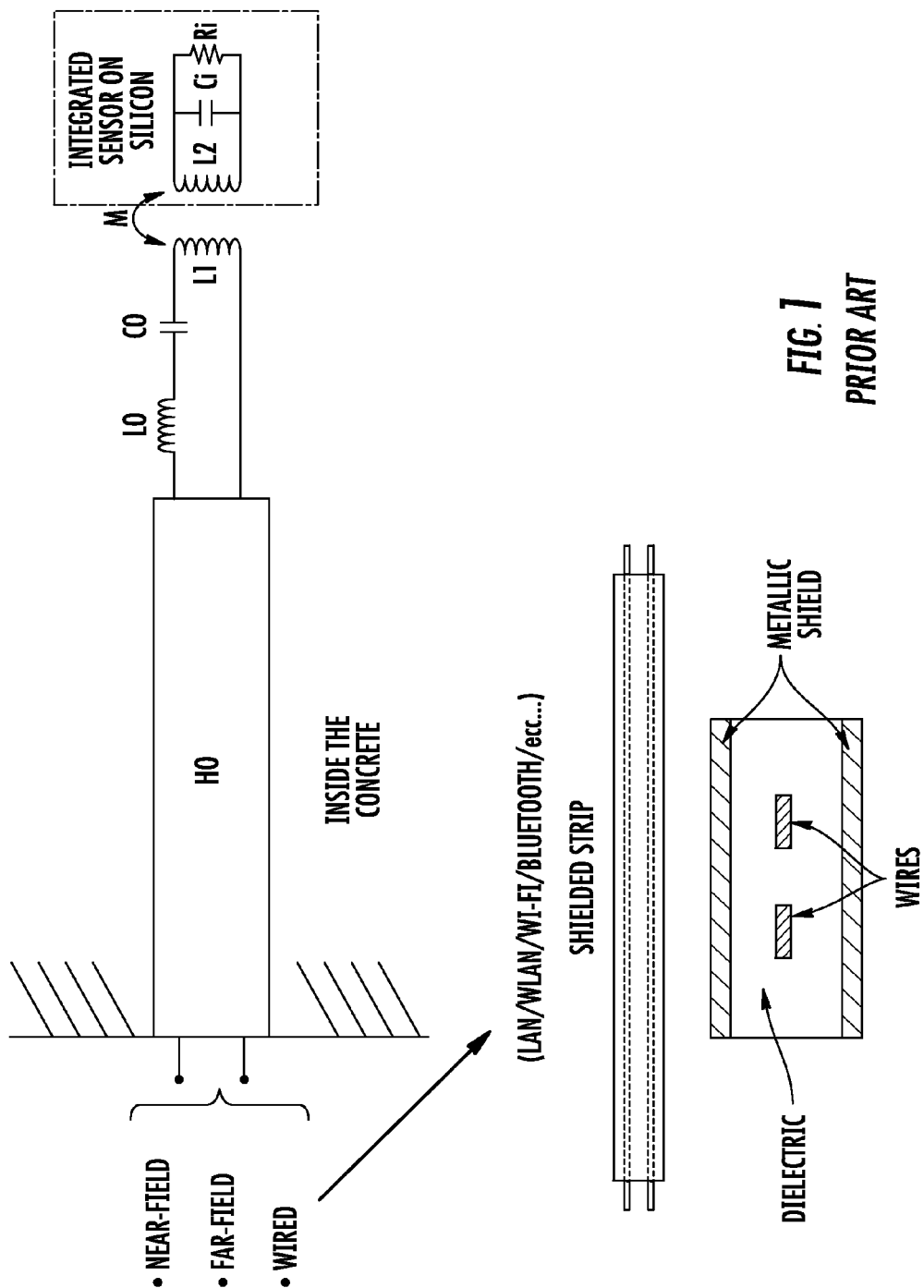
FIG. 1 is a schematic diagram of a shielded line that powers a monitoring circuit buried in a building material, disclosed in Italian patent application No. VA2010A000097, as in the prior art.
Figure 2:
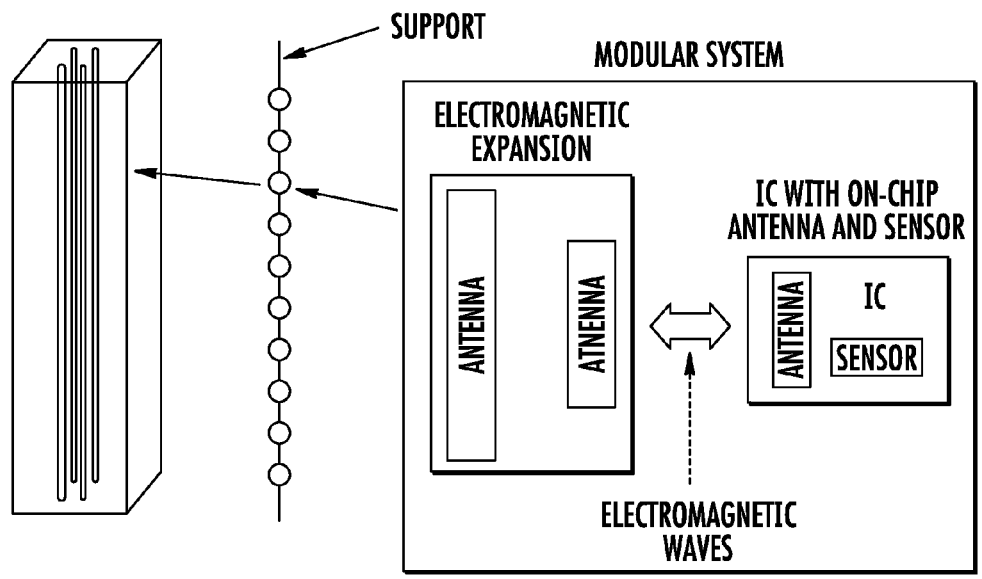
FIG. 2 is a schematic diagram depicting monitoring circuits connected to a same linear support and buried in a building material, disclosed in Italian patent application No. MI2010A002365, as in the prior art.
Figure 3:
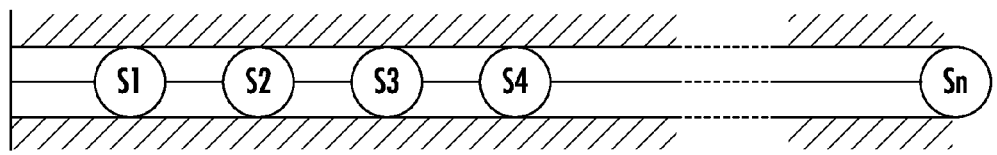
FIG. 3 is a schematic diagram depicting a monitoring device of the present disclosure embedded in a block of building material having a plurality of buried monitoring circuits coupled to a same electric line.

An embodiment of a monitoring device of this present disclosure is schematically shown in FIG. 3. The monitoring device that is depicted when buried inside a block of building material, has an electrical supply line to which monitoring circuits S1, S2, ... Sn are functionally coupled. These monitoring circuits have sensors capable of sensing at least one physical characteristic of the building material in which they are buried, and secondary inductors L2 of the internal power supply.

When the electric line is AC powered, stationary voltage and current waveforms are generated by the superposition of a progressive wave and of a reflected wave. In the field of transmission lines it is well known that this effect is maximum in electric lines that end with a short-circuit (null impedance) or with an open circuit (infinite impedance), because in these cases the electric line does not absorb active power, but only reactive power. If the lines were connected with a non-null finite impedance at their end, the above described phenomenon would still occur, but would be attenuated.

Figure 4:
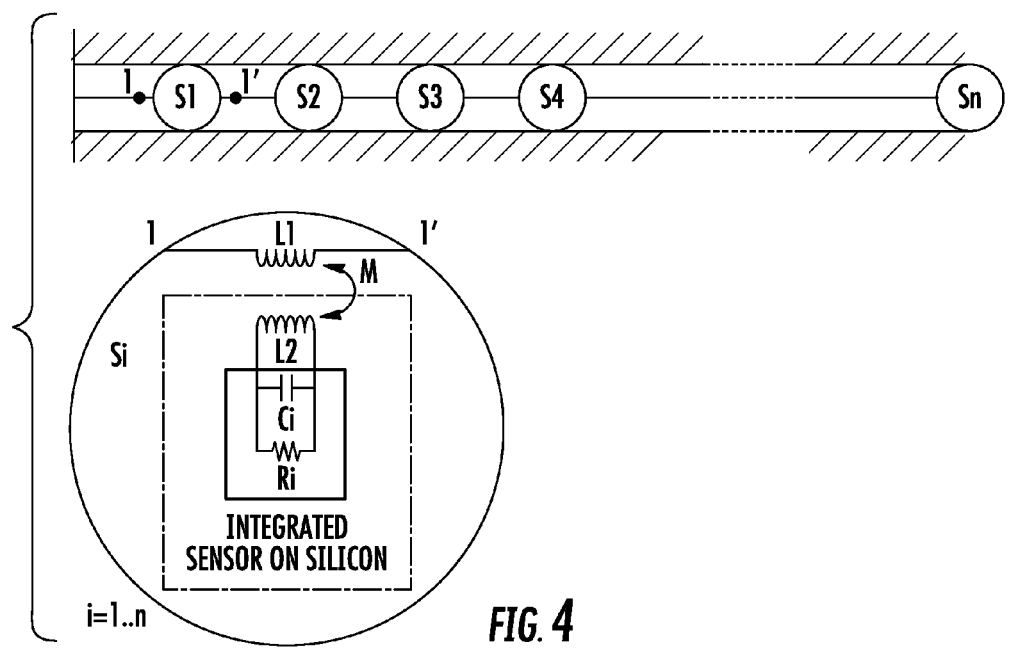
FIG. 4 is a schematic diagram illustrating a magnetic coupling between a monitoring circuit, schematically represented with its input impedance, and a respective series inductor of the electric line as in the present disclosure.

As shown in FIG. 4, the device has primary inductors L1 disposed along the electrical power supply line in correspondence with the peaks of voltage and/or current stationary waveforms, such as to be crossed by current. The monitoring circuits S1, S2, ... Sn have secondary inductors L2 magnetically coupled to respective primary inductors L1, such as to generate on its nodes an induced supply voltage of the respective circuit. Moreover, to maximize this induced supply voltage, the secondary inductors L2 may be realized such as to resonate at the working frequency with the equivalent input capacitances of the integrated circuit. By realizing in this way the monitoring device, all of its sensors may be supplied through a single electric line and without using remote powering antennas integrated in the monitoring circuits.

Figure 5:
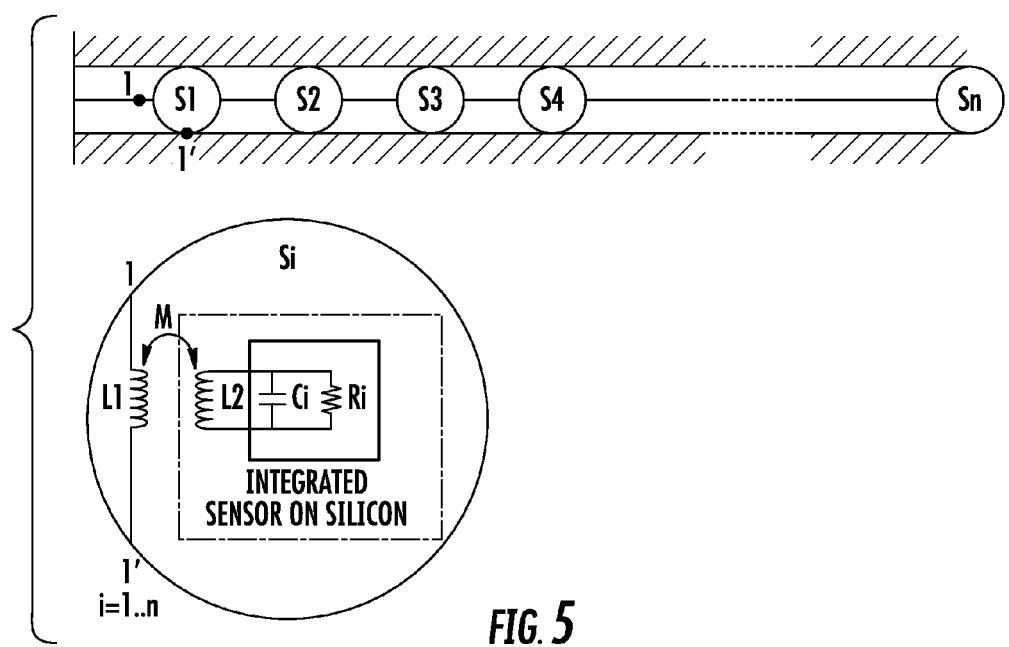
FIG. 5 is a schematic diagram illustrating a magnetic coupling between a monitoring circuit and a respective parallel inductor connected between the forward path and the return path of the electric line as in the present disclosure.

The embodiment of FIG. 5 is similar to that of FIG. 4, though in this case the primary inductors L1 are placed in correspondence with the peaks of the voltage stationary waveform and are connected in parallel with the electric supply line. Between the points 1 and 1' there is an AC voltage having an amplitude equal to the corresponding peak of the stationary waveform, thus the primary inductor L1 is crossed by an AC current that will allow powering of the corresponding monitoring circuit because of the magnetic coupling with the related secondary inductor L2.

Figure 6:
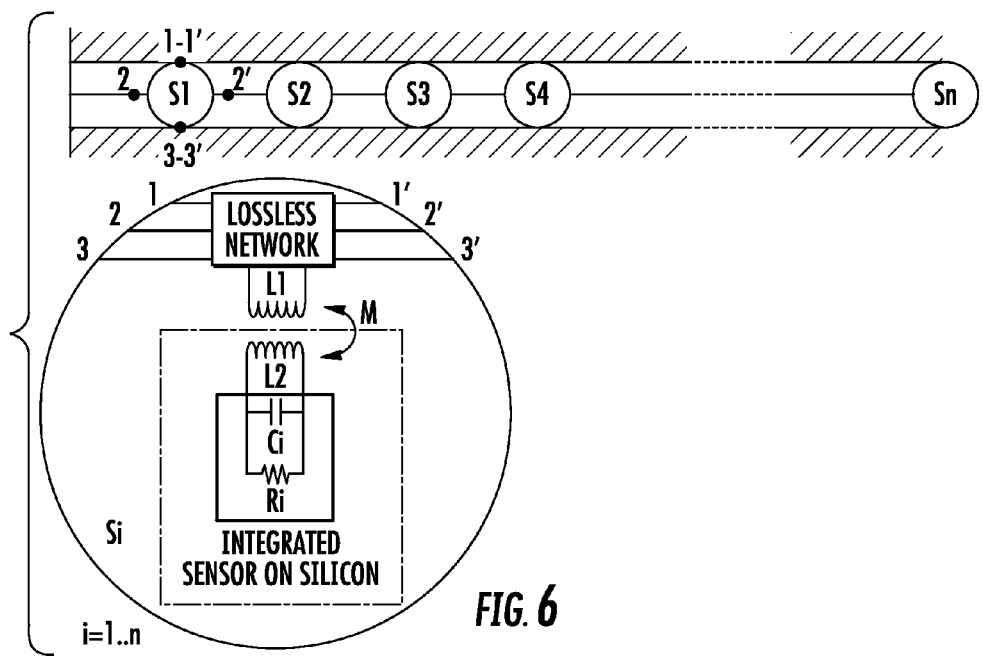
FIG. 6 is a schematic diagram showing a matching network connected to the buried electric line as in the present disclosure.

According to yet another embodiment depicted in FIG. 6, the electric supply line is equipped with lossless impedance matching networks placed in correspondence with the peaks of voltage and/or current stationary waveforms that resonate at the working frequency with the respective primary inductor L1. The working principle is the same as that discussed referring to FIGS. 4 and 5.

According to a method aspect, once the monitoring device is placed inside the structure to be monitored, the electric line is AC powered. Thus voltage and current stationary waveforms are generated with peaks located in correspondence with the primary inductors L1, that will power the sensors buried in the building material. The signals generated by the sensors and transmitted through the electric line are received, by using the magnetic coupling between the secondary inductors L2 and the respective primary inductors L1.

Figure 7:
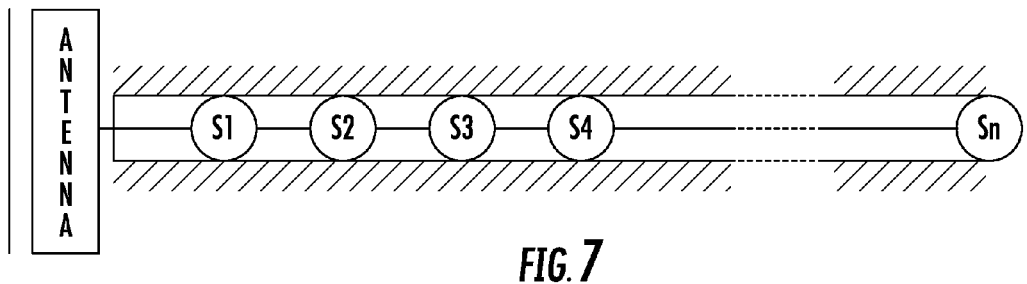
FIG. 7 is a schematic diagram showing a monitoring device of this disclosure embedded in a block of building material having a plurality of buried monitoring circuits coupled to a same electric line ending with a buried antenna for remote powering and for data transmission.

Furthermore, it is possible to realize blocks made of a building material embedding the monitoring devices described herein. Advantageously but not necessarily, the electric line ends with a remote powering and data transmission antenna buried in the block of building material, as schematically shown in FIG. 7.

Figure 8:
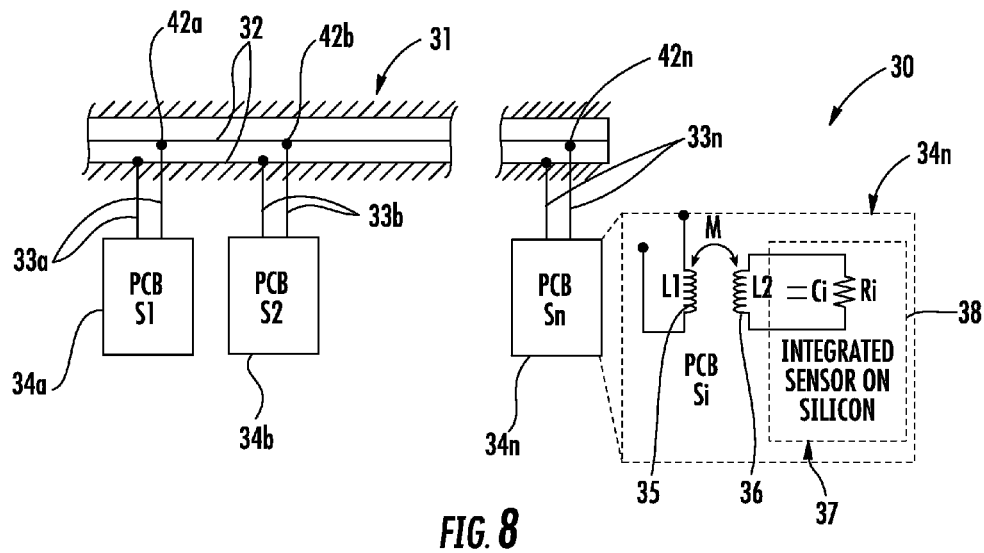
FIG. 8 is a schematic diagram of another embodiment of the monitoring device, according to the present disclosure.

Referring now additionally to FIG. 8, another embodiment of the monitoring device 30 is now described. In this embodiment of the monitoring device 30, the monitoring device is positioned in a block of building material 41. The monitoring device 30 illustratively includes an electric supply line 31 configured to be buried in the block of building material 41 and comprises a flexible main cable 32, and a plurality of flexible jumper cables 33a-33n coupled to the flexible main cable and extending outwardly therefrom. The monitoring device 30 illustratively includes a plurality of sensor devices 34a-34n configured to be buried in the block of building material 41 and coupled to respective ones of the plurality of flexible jumper cables 33a-33n.

Each sensor device 34a-34n illustratively includes a primary inductor 35 coupled to the electric supply line 31 at a position based upon peaks of at least one stationary waveform when the electric supply line is AC powered, and a monitoring circuit 37. The monitoring circuit 37 illustratively includes an integrated sensor 38, and a secondary inductor 36 magnetically coupled to the primary inductor 35 and configured to supply the integrated sensor, and communicate through the electric supply line 31.

In some embodiments, each sensor device 34a-34n comprises a connector for receiving the respective ones of the plurality of flexible jumper cables 33a-33n. In other embodiments, each sensor device 34a-34n comprises a dongle type device with a built-in jumper cable directly coupled to the flexible main cable 32.

The electric supply line 31 illustratively includes a plurality of connectors 42a-42n (e.g. coaxial T-connector, T-tap automobile connector) coupling the respective ones of the plurality of flexible jumper cables 33a-33n to the flexible main cable 32. The monitoring device 30 may further comprise an antenna (FIG. 7) coupled to the electric supply line 31 and configured to be remotely powered and transmit sensed values of at least one physical characteristic.

Figure 12:
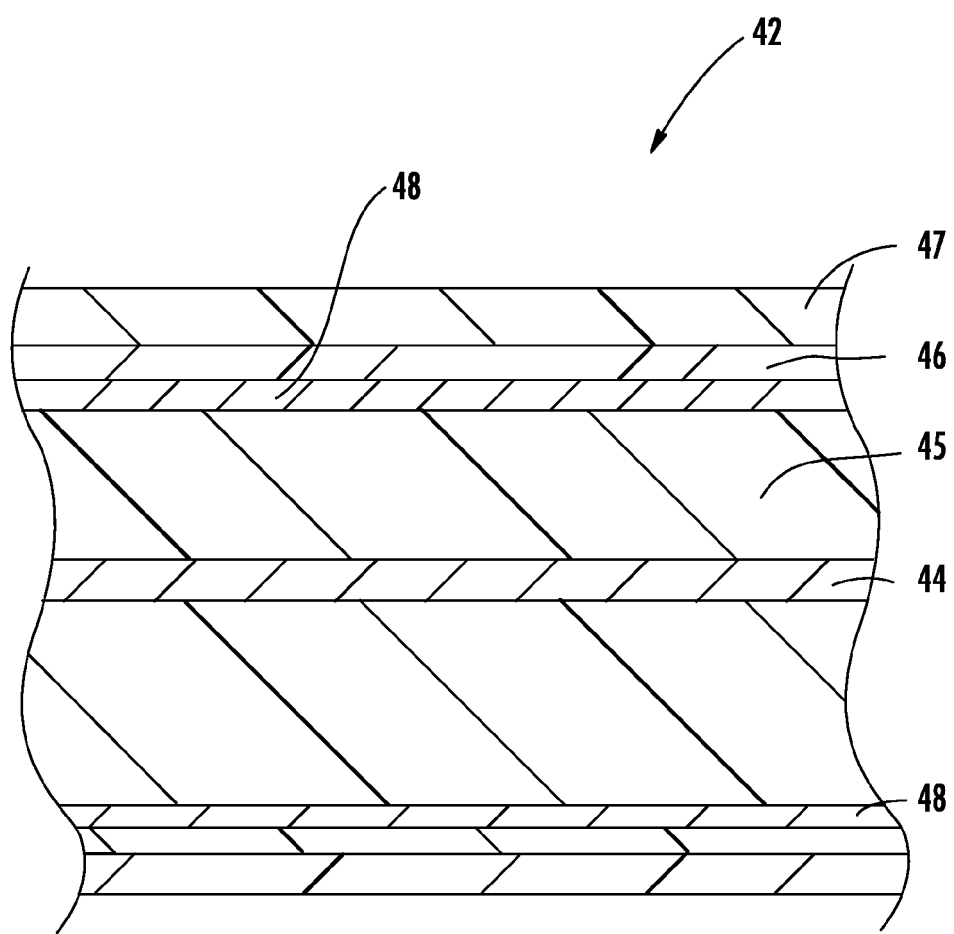
FIG. 12 is a cross-section view of a portion of an embodiment of a connector from the monitoring device of FIG. 8

In some embodiments (FIG. 12), the electric supply line 31 comprises a plurality of encapsulation layers 47 respectively surrounding the plurality of connectors 42. Also, the flexible main cable 32 and the plurality of flexible jumper cables 33a-33n may each comprise a coaxial cable portion comprising an inner conductor 44, a dielectric material 45 surrounding the inner conductor, an outer conductor 48 surrounding the dielectric material, a sheath 46 surrounding the outer conductor, and the encapsulation later 47 surrounding the sheath. For example, the encapsulation later 47 may comprise dielectric adhesive backed tape, or an epoxy resin material.

Also, at least one of the primary inductors 35 may be electrically coupled in series with the electric supply line 31 in correspondence with peaks of a current stationary waveform. At least one of the primary inductors 35 may be electrically coupled in parallel with the electric supply line 31 in correspondence with peaks of a voltage stationary waveform. The monitoring device 30 may further include a resonant network (FIG. 6) coupled to at least one of the primary inductors.

Another aspect is directed to a method for making a monitoring device 30 for a block of building material 41. The method may include providing an electric supply line 31 to be buried in the block of building material 41 and comprising a flexible main cable 32, and a plurality of flexible jumper cables 33a-33n coupled to the flexible main cable and extending outwardly therefrom. The method may include coupling a plurality of sensor devices 34a-34n to respective ones of the plurality of flexible jumper cables 33a-33n. Each sensor device 34a-34n may comprise a primary inductor 35 coupled to the electric supply line 31 at a position based upon peaks of at least one stationary waveform when the electric supply line is AC powered, and a monitoring circuit 37. The monitoring circuit 37 may include an integrated sensor 38, and a secondary inductor 36 magnetically coupled to the primary inductor 35 and to supply the integrated sensor, and communicate through the electric supply line 31.

Figure 9:
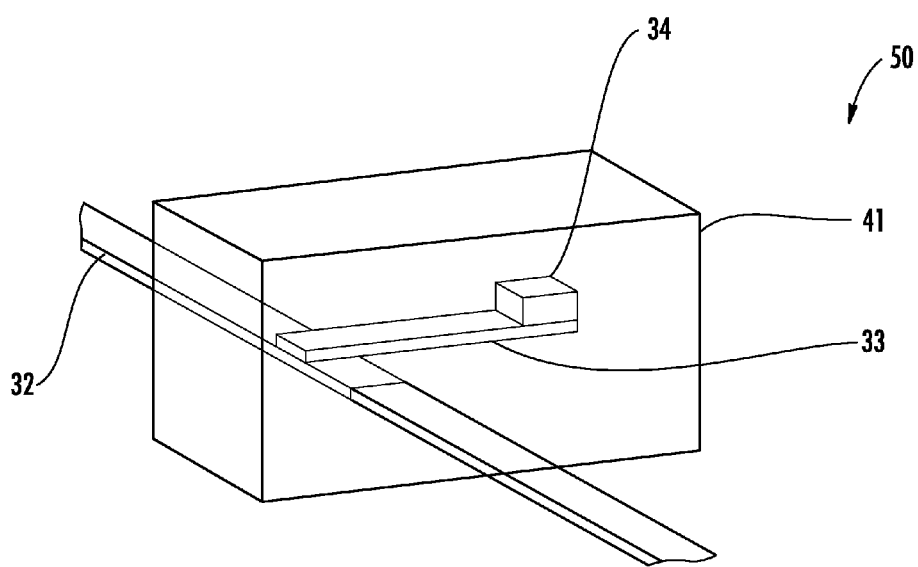
FIG. 9 is another schematic diagram of a portion of the monitoring device, according to the present disclosure.
Figure 10:
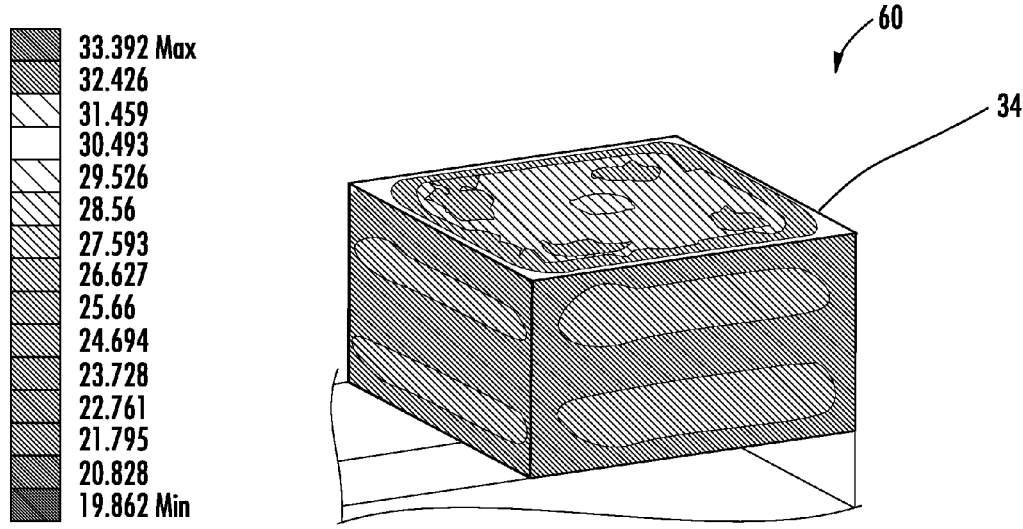
FIGS. 10-11 are stress diagrams for the monitoring device of FIG. 9.
Figure 11:
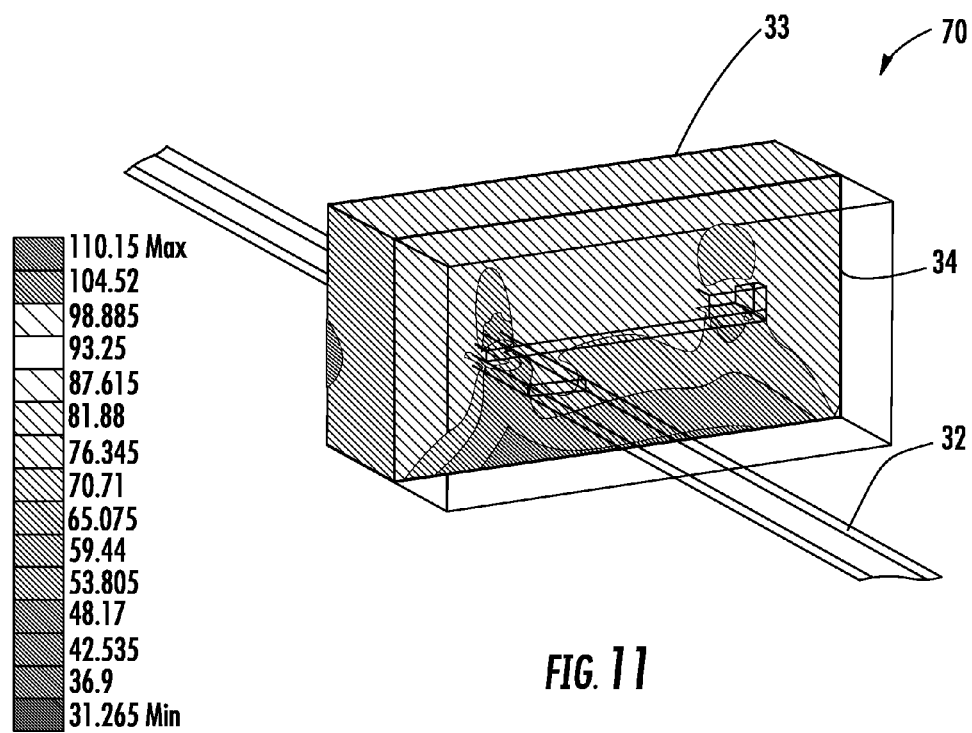

Referring now to FIGS. 9-11, stress diagrams 50, 60, 70 demonstrate the mechanical isolation of the plurality of sensor devices 34a-34n, which provides for a more accurate measurement. These mechanical simulations show the mechanical stress on sensor surface being independent (from an engineering point of view) from the electric supply line 31. Indeed, there is no mechanical coupling between the electric supply line 31 and the plurality of sensor devices 34a-34n.

Advantageously, since the electric supply line 31 is largely flexible, the monitoring device 30 may be readily installed into building material. Also, this monitoring device 30 is less expensive to manufacture than prior embodiments where the electric supply line is printed onto a substrate. Indeed, typical coaxial cable can be used for the electric supply line 31. Moreover, the modular approach of the monitoring device 30 enables the user to independently test/calibrate the electric supply line 31 and the plurality of sensor devices 34a-34n.

Many modifications and other embodiments of the present disclosure will come to the mind of one skilled in the art having the benefit of the teachings presented in the foregoing descriptions and the associated drawings. Therefore, it is understood that the present disclosure is not to be limited to the specific embodiments disclosed, and that modifications and embodiments are intended to be included within the scope of the appended claims.

That which is claimed is:

1. A monitoring device for a block of building material comprising:
    an electric supply line configured to be buried in the block of building material and comprising
        a flexible main cable, and
        a plurality of flexible jumper cables coupled to said flexible main cable and extending outwardly therefrom; and
    a plurality of sensor devices configured to be buried in the block of building material and coupled to respective ones of said plurality of flexible jumper cables, each sensor device comprising
        a primary inductor coupled to the electric supply line at a position based upon peaks of at least one stationary waveform when the electric supply line is alternating current (AC) powered, and
        a monitoring circuit comprising
            an integrated sensor, and
            a secondary inductor magnetically coupled to said primary inductor and configured to supply the integrated sensor, and communicate through the electric supply line.

2. The monitoring device of claim 1 wherein said flexible main cable and said plurality of flexible jumper cables each comprises a coaxial cable portion.

3. The monitoring device of claim 1 wherein said electric supply line comprises a plurality of connectors coupling the respective ones of said plurality of flexible jumper cables to said flexible main cable.

4. The monitoring device of claim 3 wherein each connector comprises a T-connector.

5. The monitoring device of claim 3 wherein said electric supply line comprises a plurality of encapsulation layers respectively surrounding said plurality of connectors.

6. The monitoring device of claim 1 further comprising an antenna coupled to the electric supply line and configured to be remotely powered and transmit sensed values of at least one physical characteristic.

7. The monitoring device of claim 1 wherein at least one of the primary inductors is electrically coupled in series with the electric supply line in correspondence with peaks of a current stationary waveform.

8. The monitoring device of claim 1 wherein at least one of the primary inductors is electrically coupled in parallel with the electric supply line in correspondence with peaks of a voltage stationary waveform.

9. The monitoring device of claim 1 further comprising a resonant network coupled to at least one of the primary inductors.

10. A monitoring device for a block of building material comprising:
    an electric supply line configured to be buried in the block of building material and comprising a flexible main cable,
a plurality of flexible jumper cables coupled to said flexible main cable and extending outwardly therefrom, and
a plurality of connectors coupling respective ones of said plurality of flexible jumper cables to said flexible main cable;
a plurality of sensor devices configured to be buried in the block of building material and coupled to the respective ones of said plurality of flexible jumper cables, each sensor device comprising
a primary inductor coupled to the electric supply line at a position based upon peaks of at least one stationary waveform when the electric supply line is alternating current (AC) powered, and
a monitoring circuit comprising
an integrated sensor, and
a secondary inductor magnetically coupled to said primary inductor and configured to supply the integrated sensor, and communicate through the electric supply line; and
an antenna coupled to the electric supply line and configured to be remotely powered and transmit sensed values of at least one physical characteristic.

11. The monitoring device of claim 10 wherein said flexible main cable and said plurality of flexible jumper cables each comprises a coaxial cable portion.

12. The monitoring device of claim 10 wherein each connector comprises a T-connector.

13. The monitoring device of claim 10 wherein said electric supply line comprises a plurality of encapsulation layers respectively surrounding said plurality of connectors.

14. The monitoring device of claim 10 wherein at least one of the primary inductors is electrically coupled in series with the electric supply line in correspondence with peaks of a current stationary waveform.

15. A method for making a monitoring device for a block of building material, the method comprising:
providing an electric supply line to be buried in the block of building material and comprising
a flexible main cable, and
a plurality of flexible jumper cables coupled to the flexible main cable and extending outwardly therefrom; and
coupling a plurality of sensor devices to respective ones of the plurality of flexible jumper cables, each sensor device comprising
a primary inductor coupled to the electric supply line at a position based upon peaks of at least one stationary waveform when the electric supply line is alternating current (AC) powered, and
a monitoring circuit comprising
an integrated sensor, and
a secondary inductor magnetically coupled to the primary inductor and to supply the integrated sensor, and communicate through the electric supply line.

16. The method of claim 15 wherein the flexible main cable and the plurality of flexible jumper cables each comprises a coaxial cable portion.

17. The method of claim 15 wherein the electric supply line comprises a plurality of connectors coupling the respective ones of the plurality of flexible jumper cables to the flexible main cable.

18. The method of claim 17 wherein each connector comprises a T-connector.

19. The method of claim 17 wherein the electric supply line comprises a plurality of encapsulation layers respectively surrounding the plurality of connectors.

20. The method of claim 15 further comprising coupling an antenna to the electric supply line and to be remotely powered and transmit sensed values of at least one physical characteristic.

* * * * *